US012766336B2

(12) United States Patent
Choi et al.

(10) Patent No.: US 12,766,336 B2
(45) Date of Patent: Oct. 20, 2026

(54) PATTERNED OPTICAL STIMULATION DEVICE AND METHOD

(71) Applicants: SEOUL NATIONAL UNIVERSITY R&DB FOUNDATION, Seoul (KR); KOREA UNIVERSITY RESEARCH AND BUSINESS FOUNDATION, Seoul (KR); KOREA INSTITUTE OF SCIENCE AND TECHNOLOGY, Seoul (KR)

(72) Inventors: Myunghwan Choi, Seongnam-si (KR); Seonghoon Kim, Seoul (KR); Kyuha Chong, Seoul (KR); Sungwook Yang, Seoul (KR)

(73) Assignees: SEOUL NATIONAL UNIVERSITY R&DB FOUNDATION, Seoul (KR); KOREA UNIVERSITY RESEARCH AND BUSINESS FOUNDATION, Seoul (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 243 days.

(21) Appl. No.: 18/697,219

(22) PCT Filed: Jun. 13, 2022

(86) PCT No.: PCT/KR2022/008292
§ 371 (c)(1),
(2) Date: Mar. 29, 2024

(87) PCT Pub. No.: WO2023/054836
PCT Pub. Date: Apr. 6, 2023

(65) Prior Publication Data

US 2024/0399165 A1 Dec. 5, 2024

(30) Foreign Application Priority Data

Sep. 30, 2021 (KR) ........................ 10-2021-0130104

(51) Int. Cl.
*A61N 5/06* (2006.01)
*A61B 5/00* (2006.01)

(52) U.S. Cl.
CPC .......... *A61N 5/0616* (2013.01); *A61B 5/0059* (2013.01); *A61B 5/444* (2013.01); *A61N 2005/0627* (2013.01); *A61N 2005/063* (2013.01)

(58) Field of Classification Search
CPC ....... A61B 5/00; A61B 5/0059; A61B 5/0075; A61B 5/441; A61B 5/444;
(Continued)

(56) References Cited

U.S. PATENT DOCUMENTS

| | | | |
|---|---|---|---|
| 2017/0224205 A1 | 8/2017 | Sunar et al. | |
| 2021/0059782 A1 | 3/2021 | Trulson et al. | |

FOREIGN PATENT DOCUMENTS

| | | |
|---|---|---|
| CA | 2581697 A1 | 4/2005 |
| KR | 10-2010-0013650 A | 7/2008 |

(Continued)

OTHER PUBLICATIONS

Office Action issued Mar. 17, 2025 in Korean Patent Application No. 10-2024-0063959.

(Continued)

*Primary Examiner* — Jon Eric C Morales
(74) *Attorney, Agent, or Firm* — Sughrue Mion, PLLC

(57) ABSTRACT

Disclosed are a patterned optical stimulation device and method. The patterned optical stimulation device according to one aspect includes: an imaging unit which generates a skin tissue image; a diagnosis unit which detects a region of interest from the skin tissue image and diagnoses the detected region of interest; and an optical stimulation unit which forms patterned treatment light corresponding to the
(Continued)

region of interest and irradiates the region of interest with the formed patterned treatment light.

9 Claims, 3 Drawing Sheets

(58) Field of Classification Search
CPC .... A61N 2005/0626; A61N 2005/0627; A61N 2005/063; A61N 5/0616; A61N 5/062
See application file for complete search history.

(56) References Cited

FOREIGN PATENT DOCUMENTS

| | | | |
|---|---|---|---|
| KR | 10-2010-0120364 | A | 11/2010 |
| KR | 10-1015881 | B1 | 2/2011 |
| KR | 10-2012-0066286 | A | 6/2012 |
| KR | 10-1454271 | B1 | 7/2012 |
| KR | 10-2014-0056083 | A | 5/2014 |
| KR | 10-2018-0085250 | A | 7/2018 |
| KR | 10-1901181 | B1 | 9/2018 |
| KR | 10-2021-0006792 | A | 1/2021 |

OTHER PUBLICATIONS

Korean Office Action for Korean Application No. 10-2021-0130104 dated Jun. 8, 2023.
Korean Decision of Rejection for Korean Application No. 10-2021-0130104 dated Oct. 11, 2023.
Korean Notification of Decision Re-examination for Korean Application No. 10-2021-0130104 dated Feb. 14, 2024.
Korean Decision of declination for Korean Application No. 10-2021-0130104 dated Feb. 14, 2024.
International Search Report for PCT/KR2022/008292 dated Dec. 20, 2022.
Written Opinion for PCT/KR2022/008292 dated Dec. 20, 2022.
Extended European Search Report issued Feb. 28, 2025 in Application No. 22876611.9.

[FIG. 1]
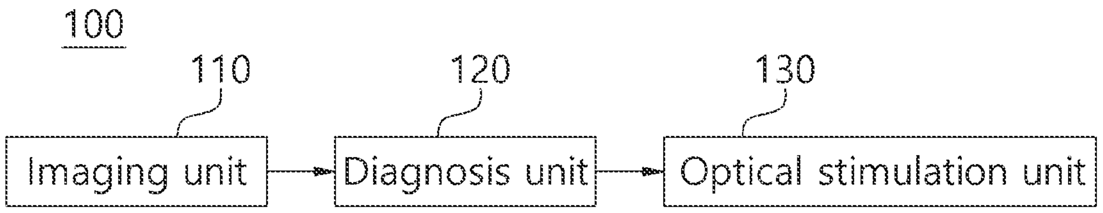
[FIG. 2]
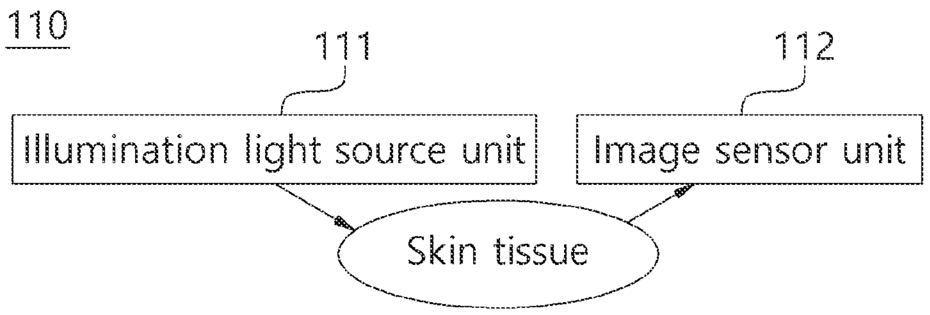
[FIG. 3]
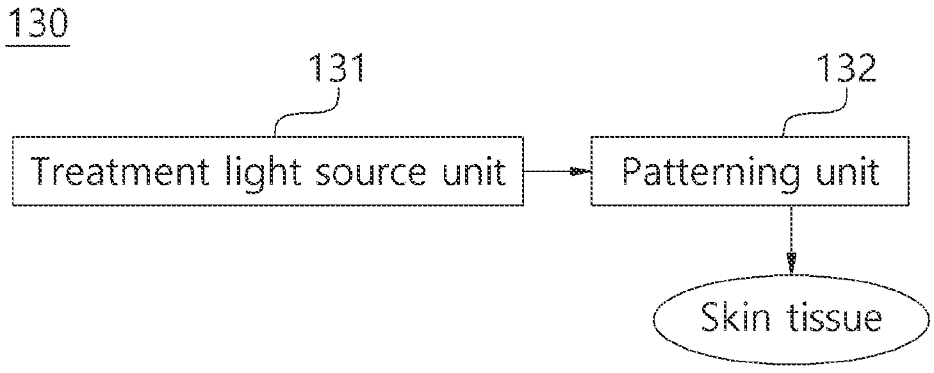

[FIG. 4]
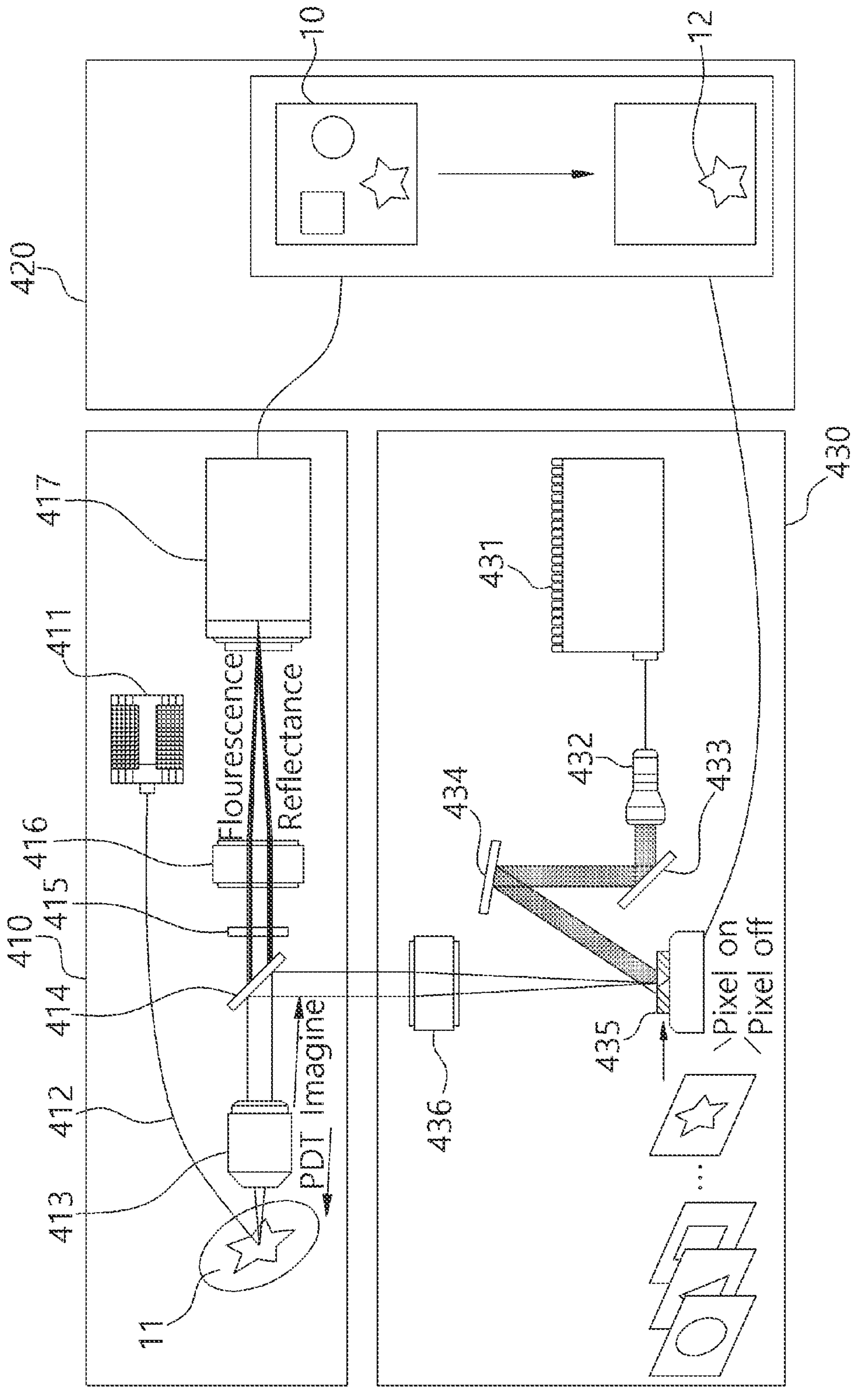

[FIG. 5]
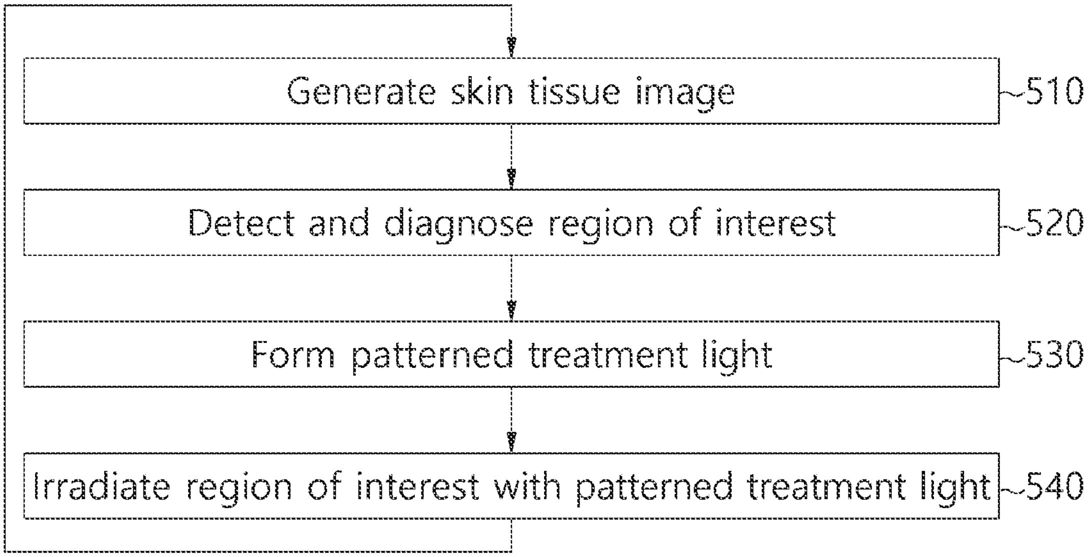
[FIG. 6]
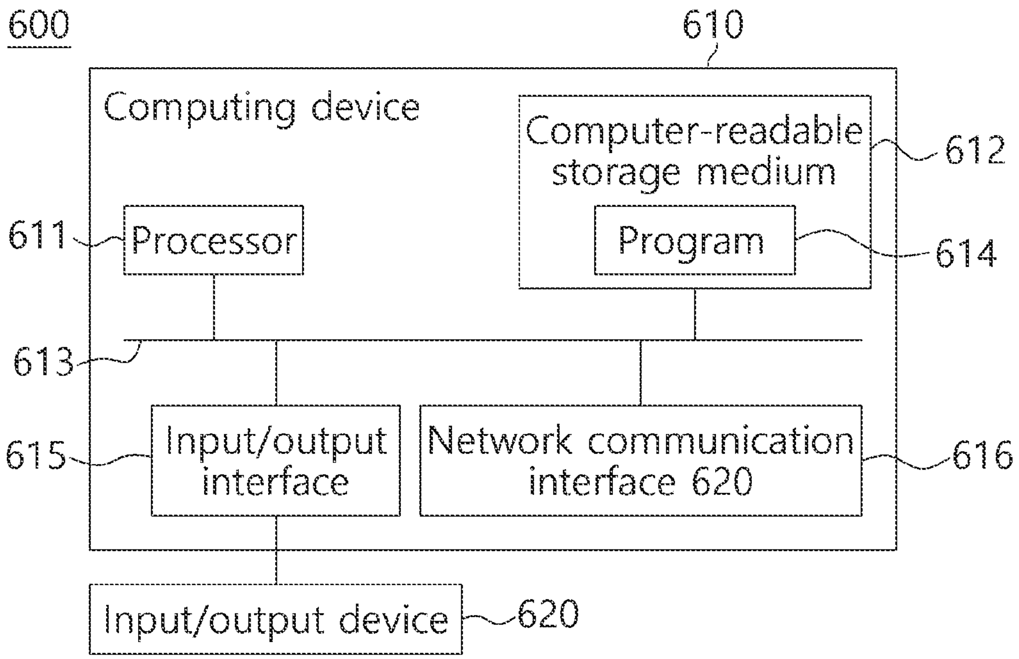

PATTERNED OPTICAL STIMULATION DEVICE AND METHOD

CROSS REFERENCE TO RELATED APPLICATIONS

This application is a National Stage of International Application No. PCT/KR2022/008292 filed Jun. 13, 2022, claiming priority based on Korean Patent Application No. 10-2021-0130104 filed Sep. 30, 2021.

TECHNICAL FIELD

The present invention relates to a phototherapy technique.

Background Art

Photodynamic therapy is a technique of selectively removing cancer cells by activating a photosensitizer in a local region using light. Although photosensitizers used in clinical practices have been developed to be transferred to the cancer cells with relatively high efficiency, there is no technique capable of completely and accurately transferring the photosensitizer only to the cancer cells up to now. Therefore, the photosensitizer is inevitably distributed even in normal cells.

Meanwhile, in the case of precise organs such as brains, it is often difficult to perform surgery, and in order to prevent recurrence even after surgery, a process of additionally removing residual cancer cells is required. The photodynamic therapy is used to remove cancer cells distributed in a size of the cell level, but in order to minimize damage to sensitive nerve tissues in the brain, by reducing the intensity of light and irradiating brain tissues with the light for a long period of time, the required amount of light is delivered. Therefore, the time for exposing the brain tissues to an outside is inevitably increased, which affects the safety and effectiveness of the surgical operation and the patient's recovery.

Therefore, it is necessary to develop a technique that reduces surgical operation time by locally irradiating only a region requiring the surgical operation with high-intensity light, and prevents the normal tissues from being unnecessary irradiated with the light.

SUMMARY OF INVENTION

Problems to be Solved by Invention

An object of the present invention is to provide a patterned optical stimulation device and method, which are capable of irradiating a region of interest with patterned light which is formed corresponding to the region of interest through real-time analysis of skin images.

Means for Solving Problems

To achieve the above object, according to an aspect of the present invention, there is provided a patterned optical stimulation device including: an imaging unit configured to generate a skin tissue image; a diagnosis unit configured to detect a region of interest from the skin tissue image and diagnose the detected region of interest; and an optical stimulation unit configured to form patterned treatment light corresponding to the region of interest, and irradiate the region of interest with the formed patterned treatment light.

The imaging unit may include: an illumination light source unit configured to emit illumination light to the skin tissue; and an image sensor unit configured to receive reflected light, scattered light, or fluorescence from the skin tissue to generate a skin tissue image.

The region of interest may include tumor, dermatitis, acne, tattoos, dots, blood vessels, wrinkles, pores, and sweat glands.

The optical stimulation unit may include: a treatment light source unit configured to output treatment light by determining a treatment light parameter based on diagnosis results in the region of interest; and a patterning unit configured to pattern the output treatment light based on detection results in the region of interest to form patterned treatment light corresponding to the region of interest.

The patterning unit may include a spatial light modulator (SLM) or a digital micromirror device (DMD).

The therapeutic light parameter may include a wavelength, an intensity, an output time or duration of the treatment light.

According to another aspect of the present invention, there is provided a patterned optical stimulation method including: generating a skin tissue image; detecting a region of interest from the skin tissue image and diagnosing the detected region of interest; forming patterned treatment light corresponding to the region of interest; and irradiating the region of interest with the formed patterned treatment light.

The step of generating the skin tissue image may include: emitting illumination light to the skin tissue; and receiving reflected light, scattered light, or fluorescence from the skin tissue to generate a skin tissue image.

The region of interest may include tumor, dermatitis, acne, tattoos, dots, blood vessels, wrinkles, pores, and sweat glands.

The step of forming the patterned treatment light may include: outputting treatment light by determining a treatment light parameter based on diagnosis results in the region of interest; and patterning the output treatment light based on detection results in the region of interest to form patterned treatment light corresponding to the region of interest.

The therapeutic light parameter may include a wavelength, an intensity, an output time or duration of the treatment light.

Advantageous Effects

According to the embodiments, it is possible to reduce surgical operation time by irradiating only a region requiring a surgical operation with high-intensity light, and prevent the normal tissues from being unnecessary irradiated with the light.

In addition, the shape of a light pattern, intensity, and treatment/surgical operation time can be automatically determined based on real-time feedback, such that the effect of phototherapy or surgical operation may be maximized.

Further, the exposure time of an affected area can be minimized in some tumor treatments, such that it may have a positive effect on the patient's recovery.

Furthermore, the detection and diagnosis in the region of interest and the treatment light irradiation are performed automatically according to real-time feedback, such that the advanced surgical operation ability of an operator is not required, and thereby the inventive device and method may be quickly and safely applied to the actual clinical practices.

BRIEF DESCRIPTION OF DRAWINGS

FIG. 1 is a block diagram illustrating a patterned optical stimulation device according to an exemplary embodiment.

FIG. 2 is a block diagram illustrating an imaging unit according to an exemplary embodiment.

FIG. 3 is a block diagram illustrating an optical stimulation unit according to an exemplary embodiment.

FIG. 4 is a schematic structural diagram of a patterned optical stimulation device according to another exemplary embodiment.

FIG. 5 is a diagram illustrating a patterned optical stimulation method according to an exemplary embodiment.

FIG. 6 is a block diagram for illustrating and describing a computing environment including a computing device suitable for use in exemplary embodiments.

MODE FOR CARRYING OUT INVENTION

Hereinafter, embodiments will be described in detail with reference to the accompanying drawings. In denoting reference numerals to components of respective drawings, it should be noted that the same components will be denoted by the same reference numerals although they are illustrated in different drawings. Further, in description of preferred embodiments of the present invention, the publicly known functions and configurations related to the present invention, which are verified to be able to make the purport of the present invention unnecessarily obscure will not be described in detail.

Meanwhile, in respective steps, each of the steps may occur differently from the specified order unless a specific order is clearly described in the context. That is, each of the steps may be performed in the same order as the specified order, may be performed substantially simultaneously, or may be performed in the reverse order.

Further, wordings to be described below are defined in consideration of the functions in the present invention, and may differ depending on the intentions of a user or an operator or custom. Accordingly, such wordings should be defined on the basis of the contents of the overall specification.

It will be understood that, although the terms first, second, etc. may be used herein to describe various components, but these components should not be limited by these terms. These terms are used only to distinguish one component from other components. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

In addition, a division of the configuration units in the present disclosure is intended for ease of description and divided only by the main function set for each configuration unit. That is, two or more of the configuration units to be described below may be combined into a single configuration unit or formed by two or more of divisions by function into more than a single configuration unit. Further, each of the configuration units to be described below may additionally perform a part or all of the functions among functions set for other configuration units other than being responsible for the main function, and a part of the functions among the main functions set for each of the configuration units may be exclusively taken and certainly performed by other configuration units. Each of the configuration units to be described below may be implemented as hardware or software, or may be implemented as a combination of hardware and software.

FIG. 1 is a block diagram illustrating a patterned optical stimulation device according to an exemplary embodiment, FIG. 2 is a block diagram illustrating an imaging unit according to an exemplary embodiment, and FIG. 3 is a block diagram illustrating an optical stimulation unit according to an exemplary embodiment.

Referring to FIGS. 1 to 3, a patterned optical stimulation device 100 according to an exemplary embodiment may include an imaging unit 110, a diagnosis unit 120, and an optical stimulation unit 130.

The imaging unit 110 may generate a skin tissue image. To this end, the imaging unit 110 may include an illumination light source unit 111 and an image sensor unit 112.

The illumination light source unit 111 may emit illumination light to a skin tissue. Here, the illumination light may include infrared rays, visible rays, ultraviolet rays, X-rays, and the like, but it is not limited thereto.

According to an embodiment, the illumination light source unit 111 may include one or more light sources for emitting illumination lights having the same or different wavelengths to the skin tissue. The light source may be consist of a light emitting diode (LED), a laser diode, a lamp or the like.

The image sensor unit 112 may generate a skin tissue image by receiving reflected light, scattered light, or fluorescence from the skin tissue. Here, the reflected light, scattered light, or fluorescence may include a pathological signal in skin tissue. For example, the pathological signal in the skin tissue may include a selectively transferred fluorescent marker signal, a photosensitizer signal for photodynamic therapy, a spectral reflectance-based signal for the pathological tissue and the like.

According to an embodiment, the image sensor unit 112 may include a point detector (e.g., a photomultiplier tube, photodiode, silicon photomultiplier, single-photon avalanche photodiode, phototransistor, etc.), a charge-coupled device (CCD), or a complementary metal-oxide semiconductor (CMOS) and the like.

The diagnosis unit 120 may analyze the skin tissue image to detect a region of interest (ROI) and diagnose the detected region of interest. Here, the region of interest is a pathological tissue region, and may include lesions (e.g., tumor, dermatitis, acne, etc.) and regions for cosmetic dermatology treatment (e.g., tattoos, dots, blood vessels, wrinkles, pores, sweat glands, etc.).

According to an embodiment, the diagnosis unit 120 may perform detection and diagnosis in the region of interest based on skin tissue image information using features of signals observed in the pathological tissues. For example, the diagnosis unit 120 may use a signal intensity or shape distribution-based thresholding algorithm, or a machine learning algorithm.

The optical stimulation unit 130 may form patterned treatment light corresponding to the region of interest based on detection and diagnosis results in the region of interest, and may irradiate the region of interest with the formed patterned treatment light. To this end, the optical stimulation unit 130 may include a treatment light source unit 131 and a patterning unit 132.

The treatment light source unit 131 may output the treatment light by determining a treatment light parameter based on the diagnosis results in the region of interest. Here, the treatment light may include infrared rays, visible rays, ultraviolet rays, and the like, and the treatment light parameter may include a wavelength of the treatment light, an intensity of the treatment light, and an output time/duration of the treatment light, but they are not limited thereto.

According to an embodiment, the treatment light source unit 131 may include one or more light sources for outputting treatment lights having the same or different wavelengths. The light source may be consist of a light emitting diode (LED), a laser diode, a lamp or the like.

The patterning unit 132 may pattern the treatment light output from the treatment light source unit 131 based on the detection results in the region of interest to form patterned treatment light corresponding to the region of interest.

According to an embodiment, the patterning unit 132 may include, for example, a spatial light modulator (SLM), a digital micromirror device (DMD), a scanner such as galvanometers, acousto-/electro-optic deflectors, etc., which can pattern the light output from the treatment light source unit 131 to output the patterned light to an outside.

As used herein, patterning of light may mean patterning a shape that follows the shape of a region to be irradiated with light as it is, and the patterned treatment light corresponding to the region of interest may mean treatment light which is formed through patterning of the shape that follows the shape of the region of interest as it is. For example, when the shape of the region of interest is a "star" shape, the patterning unit 132 may form patterned treatment light having a "star" shape of substantially the same size as the "star" shape of the region of interest.

According to an embodiment, a process of generating a skin tissue image, a process of detecting and diagnosing the region of interest, and a process of irradiating the region of interest with the patterned therapeutic light may be conducted by a closed loop. For example, at a first point in time, the imaging unit 110 may generate a first skin tissue image, the diagnosis unit 120 may analyze the first skin tissue image to extract and diagnose a first region of interest, and the optical stimulation unit 130 may form patterned treatment light corresponding to the first region of interest to irradiate the first region of interest with the formed patterned treatment light. Thereafter, at a second point in time, the imaging unit 110 may generate a second skin tissue image, the diagnosis unit 120 may analyze the second skin tissue image to extract and diagnose a second region of interest identical to the first region of interest, and the optical stimulation unit 130 may form patterned treatment light corresponding to the second region of interest to irradiate the second region of interest with the formed patterned treatment light. By repeatedly performing these processes, even when the skin tissue moves or the patterned optical stimulation device 100 moves, it is possible to selectively irradiate only the pathological tissue with the patterned treatment light through real-time feedback. In addition, it is possible to adjust the treatment light parameter in real time based on the real-time diagnosis results.

According to an embodiment, the patterned optical stimulation device 100 may be implemented as a separate handheld device or may be implemented as one component of a large imaging device by being mounted on the large imaging device.

FIG. 4 is a schematic structural diagram of a patterned optical stimulation device according to another exemplary embodiment.

Referring to FIG. 4, a patterned optical stimulation device 400 according to another exemplary embodiment may include an imaging unit 410, a diagnosis unit 420 and an optical stimulation unit 430.

The imaging unit 410 may include an illumination light source 411 and an optical fiber 412 connected to the illumination light source 411 to transmit illumination light to a skin tissue (sample). In addition, the imaging unit 410 may include one or more lenses 413 and 416, a mirror 414, a filter 415 and an image sensor 417. Reflected light, scattered light, or fluorescence from the skin tissue may be collected through the first lens 413, and the collected reflected light, scattered light, or fluorescence may be transferred to the image sensor 417 through the mirror 414, the filter 415, and the second lens 416, thus to be used to generate a skin tissue image 10.

The diagnosis unit 420 may extract and diagnose a region of interest 11 by analyzing the skin tissue image 10 generated by the image sensor 417.

The optical stimulation unit 430 may include a treatment light source 431 which outputs treatment light, a beam expander 432 which expands a diameter of the output treatment light, one or more mirrors 433 and 434, a patterning unit 435 which patterns the treatment light to form patterned treatment light corresponding to the region of interest 11, and a third lens 436.

The treatment light output from the treatment light source 431 may have a diameter expanded through the beam expander 432, and the expanded treatment light may be transferred to the patterning unit 435 through one or more mirrors 433 and 434. The patterning unit 435 may form patterned treatment light corresponding to the region of interest 11 based on a pattern or shape 12 of the region of interest 11, and may emit it to the region of interest 11 through the third lens 436, the mirror 414 and the first lens 413.

According to an embodiment, the first lens 413 may be an objective lens, and the second lens 416 and the third lens 436 may be tube lenses.

Meanwhile, according to an embodiment, when the image sensor 417 includes a point detector, a scanner may be included between the first lens 413 and the second lens 416.

FIG. 5 is a diagram illustrating a patterned optical stimulation method according to an exemplary embodiment.

The patterned optical stimulation method of FIG. 5 may be performed by the patterned optical stimulation devices 100 and 400 shown in FIG. 1 or 4.

Referring to FIG. 5, the patterned optical stimulation device may generate a skin tissue image (510). For example, the patterned optical stimulation device may generate a skin tissue image by emitting illumination light to a skin tissue and receiving the reflected light, scattered light, or fluorescence from the skin tissue. Here, the illumination light may include infrared rays, visible rays, ultraviolet rays, X-rays, and the like, but it is not limited thereto.

According to one embodiment, the reflected light, scattered light, or fluorescence may include a pathological signal in skin tissue. For example, the pathological signal in the skin tissue may include a selectively transferred fluorescent marker signal, a photosensitizer signal for photodynamic therapy, a spectral reflectance-based signal for the pathological tissue and the like.

The patterned optical stimulation device may analyze the skin tissue image to detect a region of interest (ROI) and diagnose the detected region of interest (520). Here, the region of interest is a pathological tissue region, and may include lesions (e.g., tumor, dermatitis, acne, etc.) and regions for cosmetic dermatology treatment (e.g., tattoos, dots, blood vessels, wrinkles, pores, sweat glands, etc.).

According to an embodiment, the patterned optical stimulation device may perform detection and diagnosis in the region of interest based on skin tissue image information using features of signals observed in the pathological tissues. For example, the patterned optical stimulation device may use a signal intensity or shape distribution-based thresholding algorithm, or a machine learning algorithm.

The patterned optical stimulation device may form patterned treatment light corresponding to the region of interest based on detection and diagnosis results in the region of interest (530). For example, the patterned optical stimulation device may output the treatment light by determining a treatment light parameter based on the diagnosis results in the region of interest, and may pattern the output treatment light based on the detection results in the region of interest to form patterned treatment light corresponding to the region of interest. Here, the treatment light may include infrared rays, visible rays, ultraviolet rays, and the like, and the treatment light parameter may include a wavelength of the treatment light, an intensity of the treatment light, and an output time/duration of the treatment light, but they are not limited thereto.

As used herein, patterning of light may mean patterning a shape that follows the shape of a region to be irradiated with light as it is, and the patterned treatment light corresponding to the region of interest may mean treatment light which is formed through patterning of the shape that follows the shape of the region of interest as it is. For example, when the shape of the region of interest is a “star” shape, the patterning unit 132 may form patterned treatment light having a “star” shape of substantially the same size as the “star” shape of the region of interest.

The patterned optical stimulation device may repeatedly perform the steps of: irradiating the region of interest with the patterned treatment light (540), and generating a skin tissue image again by returning to step 510; detecting and diagnosing the region of interest (520); forming patterned treatment light (530); and irradiating the region of interest with the patterned treatment light (540) again until predetermined end conditions are satisfied.

As described above, by repeatedly performing the step of generating the skin tissue image (510), the step of detecting and diagnosing the region of interest (520), the step of the forming the patterned treatment light formation (530), and the step of irradiating the region of interest with the formed patterned treatment light (540), even when the skin tissue moves or the patterned optical stimulation device moves, it is possible to selectively irradiate only the pathological tissue with the patterned treatment light through real-time feedback. In addition, it is possible to adjust the treatment light parameter in real time based on the real-time diagnosis results.

FIG. 6 is a block diagram for illustrating and describing a computing environment including a computing device suitable for use in exemplary embodiments. In the illustrated embodiment, the respective configuration units may have different functions and capabilities other than those described below, and the computing environment may also include additional configuration units other than those described below.

A computing environment 600 illustrated in FIG. 6 may include a computing device 610. The computing device 610 may be an embodiment of the respective configuration units shown in FIGS. 1 to 5.

The computing device 610 may include at least one processor 611, a computer-readable storage medium 612 and a communication bus 613. The processor 611 may cause the computing device 610 to operate according to the above-described exemplary embodiments. For example, the processor 611 may execute one or more programs 614 stored in the computer-readable storage medium 612. The one or more programs 614 may include one or more computer-executable instructions. When executed by the processor 611, the computer-executable instructions may be configured to cause the computing device 610 to perform operations according to the exemplary embodiments.

The computer-readable storage medium 612 may store computer-executable instructions or program code, program data, and/or other suitable type of information. The program 614 stored in the computer-readable storage medium 612 may include a set of instructions executable by the processor 611. According to one embodiment, the computer-readable storage medium 612 may be a memory (a volatile memory, such as a random access memory, a non-volatile memory, or a suitable combination thereof), one or more magnetic disk storage devices, optical disk storage devices, flash memory, other types of storage medium accessed by the computing device 610 and capable of storing desired information, or a suitable combination thereof.

The communication bus 613 may connect various other configuration units of the computing device 610 including the processor 611 and the computer-readable storage medium 612 with each other.

The computing device 610 may also include one or more input/output interfaces 615 and one or more network communication interfaces 616, which provide interfaces for one or more input/output devices 620. The input/output interface 615 and the network communication interface 616 may be connected to the communication bus 613. The input/output device 620 may be connected to other configuration units of the computing device 610 through the input/output interface 615. The input/output device 620 may include, for example, a pointing device (such as a mouse or trackpad), a keyboard, a touch input device (such as a touchpad or a touchscreen), a voice or sound input device, various types of sensor devices, and/or input devices such as a photographing device, and/or output devices such as a display device, printer, speakers and/or network card. The input/output device 620 may be included in the computing device 610 as one configuration unit constituting the computing device 610 or may be connected to the computing device 610 as a separate device distinct from the computing device 610.

The above-described embodiments of the present invention may be implemented as a computer-readable code in a computer-readable recording medium. The computer-readable recording medium may include all types of recording devices for storing data that can be read by a computer system. Examples of computer-readable recording medium may include ROM, RAM, CD-ROM, magnetic tape, floppy disk, optical disk and the like. Further, the computer-readable recording medium may be distributed over a computer system connected by a network, and written and implemented in computer-readable code that can be read by the computer in a distributed manner.

The present invention has been described with reference to the preferred embodiments above, and it will be understood by those skilled in the art that various modifications may be made within the scope without departing from essential characteristics of the present invention. Accordingly, it should be interpreted that the scope of the present invention is not limited to the above-described embodiments, and other various embodiments within the scope equivalent to those described in the claims are included within the present invention.

The invention claimed is:

1. A patterned optical stimulation device comprising:

an imaging unit configured to generate a skin tissue image;

a diagnosis unit configured to detect a region of interest from the skin tissue image and diagnose the detected region of interest; and an optical stimulation unit configured to form patterned treatment light corresponding to the region of interest, and irradiate the region of interest with the formed patterned treatment light, wherein the imaging unit comprises:

an illumination light source unit configured to emit illumination light to a skin tissue; and an image sensor unit configured to receive reflected light, scattered light, or fluorescence from the skin tissue, and to generate a skin tissue image by using pathological signals in the skin tissue, the pathological signals being included in the reflected light, the scattered light, or the fluorescence, wherein the pathological signals include at least one of a selectively transferred fluorescent marker signal, a photosensitizer signal for photodynamic therapy, or a spectral reflectance-based signal for the skin tissue, and wherein the optical stimulation unit is configured to pattern the treatment light based on detection results of the region of interest, such that the patterned treatment light has a shape that corresponds one-to-one with the shape of the region of interest.

2. The patterned optical stimulation device according to claim 1, wherein the region of interest includes tumor, dermatitis, acne, tattoos, dots, blood vessels, wrinkles, pores, and sweat glands.

3. The patterned optical stimulation device according to claim 1, wherein the optical stimulation unit comprises:

a treatment light source unit configured to output treatment light by determining a treatment light parameter based on diagnosis results in the region of interest; and a patterning unit configured to pattern the output treatment light based on detection results in the region of interest to form patterned treatment light corresponding to the region of interest.

4. The patterned optical stimulation device according to claim 3, wherein the patterning unit includes a spatial light modulator (SLM) or a digital micromirror device (DMD).

5. The patterned optical stimulation device according to claim 3, wherein the therapeutic light parameter includes a wavelength, an intensity, an output time or duration of the treatment light.

6. A patterned optical stimulation method comprising:

generating a skin tissue image;

detecting a region of interest from the skin tissue image and diagnosing the detected region of interest;

forming patterned treatment light corresponding to the region of interest; and irradiating the region of interest with the formed patterned treatment light, wherein the generating the skin tissue image comprises:

receiving reflected light, scattered light, or fluorescence from skin tissue, and generating the skin tissue image by using pathological signals in the skin tissue, the pathological signals being included in the reflected light, the scattered light, or the fluorescence, wherein the pathological signals include at least one of a selectively transferred fluorescent marker signal, a photosensitizer signal for photodynamic therapy, or a spectral reflectance-based signal for the skin tissue, and wherein the forming the patterned treatment light comprises patterning the treatment light based detection results of the region of interest, such that the patterned treatment light has a shape that corresponds one-to-one with the shape of the region of interest.

7. The patterned optical stimulation method according to claim 6, wherein the region of interest includes tumor, dermatitis, acne, tattoos, dots, blood vessels, wrinkles, pores, and sweat glands.

8. The patterned optical stimulation method according to claim 6, wherein the step of forming the patterned treatment light comprises:

outputting treatment light by determining a treatment light parameter based on diagnosis results in the region of interest; and patterning the output treatment light based on detection results in the region of interest to form patterned treatment light corresponding to the region of interest.

9. The patterned optical stimulation method according to claim 8, wherein the therapeutic light parameter includes a wavelength, an intensity, an output time or duration of the treatment light.

* * * * *